(12) United States Patent
Guzman (10) Patent No.: US 12,080,185 B2
(45) Date of Patent: *Sep. 3, 2024

(54) ULTRASOUND GUIDED TRAINING SIMULATORS FOR CRYONEUROLYSIS PAIN BLOCKS

(71) Applicant: Black Cat Medical LLC, Fortville, IN (US)

(72) Inventor: Michael F. Guzman, Fortville, IN (US)

(73) Assignee: Black Cat Medical LLC, Fortville, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 18/147,022

(22) Filed: Dec. 28, 2022

(65) Prior Publication Data

US 2023/0162620 A1 May 25, 2023

Related U.S. Application Data

(63) Continuation of application No. 16/859,090, filed on Apr. 27, 2020, now Pat. No. 11,574,563.

(60) Provisional application No. 62/852,122, filed on May 23, 2019.

(51) Int. Cl.
*G09B 23/28* (2006.01)
*A61B 18/00* (2006.01)
*A61B 18/02* (2006.01)

(52) U.S. Cl.
CPC ......... *G09B 23/285* (2013.01); *G09B 23/286* (2013.01); *A61B 2018/00434* (2013.01); *A61B 2018/0293* (2013.01)

(58) Field of Classification Search
CPC ...... G09B 23/28; G09B 23/286; G09B 23/30; G09B 23/285
See application file for complete search history.

(56) References Cited

U.S. PATENT DOCUMENTS

| | | | |
|---|---|---|---|
| 6,773,263 B2 * | 8/2004 | Nicholls | G09B 23/30 434/272 |
| 7,255,565 B2 * | 8/2007 | Keegan | G09B 23/286 434/272 |
| 7,544,062 B1 * | 6/2009 | Hauschild | G09B 23/285 434/272 |
| 8,556,635 B2 | 10/2013 | Toly | |
| 8,613,621 B2 * | 12/2013 | Hendrickson | G09B 23/30 434/267 |
| 8,708,707 B2 | 4/2014 | Hendrickson et al. | |
| 8,924,334 B2 | 12/2014 | Lacey et al. | |
| 9,318,032 B2 | 4/2016 | Samosky et al. | |
| 9,378,661 B2 * | 6/2016 | East | G09B 23/30 |
| 9,449,532 B2 * | 9/2016 | Black | G09B 23/30 |
| 9,472,122 B2 | 10/2016 | Sakezles | |
| 9,953,548 B2 | 4/2018 | Fradette et al. | |

(Continued)

*Primary Examiner* — Kurt Fernstrom
(74) *Attorney, Agent, or Firm* — Woodard Emhardt Henry Reeves & Wagner (57) ABSTRACT

In certain embodiments, the present disclosure provides an anthropomorphic phantom for use with cryoneurolysis training. The anthropomorphic phantom having a body shaped to simulate a human anatomical structure. In some forms, the phantom body comprises a first material configured to simulate human soft tissue, a simulated nerve embedded within the first material, and a simulated fascial plane embedded within the first material superficial to the simulated nerve.

16 Claims, 2 Drawing Sheets

(56) References Cited

U.S. PATENT DOCUMENTS

| | | |
|---|---|---|
| 10,127,834 B2 | 11/2018 | Azevedo |
| 10,147,340 B2 * | 12/2018 | Mathur ................ G09B 23/285 |
| 10,706,743 B2 * | 7/2020 | Black .................... G09B 23/34 |
| 11,837,109 B2 * | 12/2023 | Fernandez ............. G09B 23/34 |
| 2010/0167248 A1 | 7/2010 | Ryan |
| 2010/0167249 A1 | 7/2010 | Ryan |
| 2010/0167250 A1 | 7/2010 | Ryan et al. |
| 2010/0167253 A1 | 7/2010 | Ryan et al. |
| 2014/0038153 A1 | 2/2014 | Courtoy et al. |
| 2015/0206456 A1 | 7/2015 | Foster et al. |
| 2016/0287241 A1 | 10/2016 | Azevedo |
| 2017/0287361 A1 | 10/2017 | Caron |
| 2017/0287362 A1 | 10/2017 | Caron |

\* cited by examiner

ULTRASOUND GUIDED TRAINING SIMULATORS FOR CRYONEUROLYSIS PAIN BLOCKS

CROSS-REFERENCE TO RELATED APPLICATIONS

This application is a continuation of U.S. patent application Ser. No. 16/859,090 filed Apr. 27, 2020, which claims the benefit of U.S. Provisional Application No. 62/852,122, filed May 23, 2019, which are hereby incorporated by reference.

BACKGROUND

Cryoneurolysis works by applying targeted cold to a peripheral sensory nerve, forming a precise ice ball under the skin at or near the target nerve. This freezing of the nerve immediately prevents the nerve from sending pain signals, and does not significantly damage surrounding patient tissue structures. Thus, cryoanalgesia is a reversible inhibition of the signal carrying part of the nerve. The effect on the nerve is temporary, and provides pain relief until the nerve regenerates and function is restored.

In general, target nerves suitable for Cryoneurolysis are superficial and can be difficult to locate by traditional ultrasound techniques. Current ultrasound guided regional anesthesia simulators do not have the necessary landmarks to train targeting superficial nerves with a cryoneedle.

Previous Cryoneurolysis procedures were invasive, and used large complicated machines. In one example, a device having three needle tips was utilized to achieve sufficient ice formation. These prior devices are utilized to provide a field block, in conjunction with a traditional regional anesthesia nerve block. These techniques are time consuming; requiring 30-40 minutes and can have irregular outcomes due to factors such as patient body mass index (BMI) and degree of overlap of needle placement.

Prior ultrasound training simulation phantoms were designed only for traditional nerve blocks. A need therefore exists for improved Cryoneurolysis procedures as well as methods and systems for training such procedures.

SUMMARY

The claims, and only the claims, recite the invention. In summary, it may include devices and methods for training cryoneurolysis procedures. In certain embodiments, the present disclosure provides an anthropomorphic phantom having a body shaped to simulate a human anatomical structure, the phantom body comprising a first material configured to simulate human soft tissue, a simulated nerve embedded within the first material, and a simulated fascial plane embedded within the first material superficial to the simulated nerve. In some forms, the simulated fascial plane is distinctly imageable to from the surrounding materials to simulate the sonographic characteristics of human fascial planes and surrounding anatomy. In certain embodiments, the simulated fascial plane has a tensile strength greater than the first material. In some forms, the first material may further comprise a scattering agent embedded in the material to simulate the sonographic characteristics of human soft tissue. In some forms, the simulated nerve may further comprise a scattering agent embedded in the material to simulate the sonographic characteristic s of human nervous tissue.

In certain embodiments, the simulated nerve comprises a sensor configured to detect a signal from a cryoneurolysis training needle. In some forms, the signal is a change in temperature caused by the cryoneurolysis training needle. In some forms, the change in temperature caused by the cryoneurolysis training needle comprises a colder temperature relative to the surrounding material. In some forms, a system is provided which includes a controller responsive to the sensor and configured to indicate the status of the detected signal. In certain embodiments, the controller is electrically connected to the sensor.

Further forms, objects, features, aspects, benefits, advantages, and embodiments of the present invention will become apparent from a detailed description and drawings provided herewith.

DESCRIPTION OF THE SELECTED EMBODIMENTS

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates. One embodiment of the invention is shown in great detail; although it will be apparent to those skilled in the relevant art that some features that are not relevant to the present invention may not be shown for the sake of clarity.

As used here (claims, specification, and other definitions) the following terms have the following meaning:

Articles and phrases such as, "the", "a", "an", "at least one", and "a first", "comprising", "having" and "including" here are not limited to mean only one, but rather are inclusive and open ended to also include, optionally, two or more of such elements and/or other elements. In terms of the meaning of words or terms or phrases herein, literal differences therein are not superfluous and have different meaning, and are not to be synonymous with words or terms or phrases in the same or other claims.

The term "means for" in a claim invokes 35 U.S.C. § 112(f), literally encompassing the recited function and corresponding structure and equivalents thereto. Its absence does not, unless there otherwise is insufficient structure recited for that claim element. Nothing herein or elsewhere restricts the doctrine of equivalents available to the patentee.

The term "and/or" is inclusive here, meaning "and" as well as "or". For example, "P and/or Q" encompasses, P, Q, and P with Q; and, such "P and/or Q" may include other elements as well.

The term "anesthetizing" as used herein has the meaning, a process for providing temporary loss of sensation, muscle control, and/or awareness.

The term "anterior" as used herein has the meaning, being situated nearest or toward the front of the body. With respect to the spine, the anterior is considered to be the side of the spine closest to the stomach or the throat.

The term "anteriorly" as used herein has the meaning, positioned in a location more anterior with respect to another object where the anterior refers to a position nearer to the front of a reference point.

The term "body portion" as used herein has the meaning, the main or principal part of an object. More specifically, it refers to the part of a vertebra implant that contacts the vertebral body of a neighboring vertebra.

The term "contact" as used herein has the meaning, of two objects the state or condition of physical touching. As used, contact requires at least one location where objects are directly or indirectly touching, with or without any other member(s) material in between.

The term "cranial-caudal orientation" as used herein has the meaning, in the direction along an axis running vertically toward and away from a (standing) patient's skull.

The term "cranial direction" as used herein has the meaning, in the direction toward the patient's head along the cranial-caudal axis.

The term "caudal direction" as used herein has the meaning, in the direction towards the patient's feet along the cranial-caudal axis.

The term "cryoanalgesia" (also known as cryoneurolysis) as used herein has the meaning is the reversible destruction of the signal carrying parts of a nerve. It is a small subset of treatments under the broad umbrella of cryotherapy.

The term "cryo-needle" as used herein has the meaning, a medical device having a slender, usually sharp pointed body and configured to cause freezing at the distal end, (which may include its tip, but also may be portions near to but proximal to the tip), upon activation.

The term "discectomy" as used herein has the meaning, a surgical removal of all or part of an intervertebral disc.

The term "dorsal ramus" as used herein has the meaning, the posterior division of a spinal nerve that forms the dorsal root of the nerve as it emerges from the spinal cord.

The term "Erector Spinae Plane Block" as used herein has the meaning, a paraspinal fascial plane block that involves injection of local anesthetic between the erector spinae muscle and the transverse process, thus blocking inhibiting the dorsal and/or ventral rami of the spinal nerve. Upon injection the local anesthetic spreads in a cranial and/or caudal direction inhibiting the dorsal and or ventral rami of neighboring spinal nerves along the spinal cord.

The term "facilitate" as used herein has the meaning, to aid or help accomplish an action or a process to make that action or process easier. The act of facilitation does not need to accomplish the action or process entirely on its own.

The term "front surface" as used herein has the meaning, an exterior surface which may or may not be the anterior most surface.

The term "hole" as used herein has the meaning, a hollow opening within a body, structure, or an object. It can be any shape.

The term "imageable" as used herein has the meaning, a device which is configured to allow for medical imaging of the device during use such as by computed tomography (CT), magnetic resonance (MRI), positron emission tomography (PET), fluoroscopy, and/or ultrasonography. As used herein the "imageable" device is configured to allow a user to visualize all or a portion of the device within the patient during a procedure.

The term "laminectomy" as used herein has the meaning, a surgical operation to remove the back of one or more vertebrae, usually to give access to the spinal cord or to relieve pressure on nerves.

The term "pain block" as used herein has the meaning, inhibition of one or more sensory nerves that relay pain signals to a target region of the patient's body.

The term "local anesthesia" as used herein has the meaning, a medication that causes reversible absence of pain sensation in a target area of the body. When it is used on specific nerve pathways, paralysis also can be achieved.

The term "sensory nerve" as used herein has the meaning, a nerve that carries sensory information toward the central nervous system (CNS).

The term "side" as used herein has the meaning, one of the faces on the surface of an object. An object can have multiple faces with a variety of orientations. For example, an object may have a front side, a bottom side, a back side, or a top side.

The term "spinal fusion" as used herein has the meaning, a neurosurgical or orthopedic surgical technique that joins two or more vertebrae. This procedure can be performed at any level in the spine and prevents any movement between the fused vertebrae. Spinal fusion may also be called spondylodesis or spondylosyndesis.

The term "spinal surgery" as used herein has the meaning, any surgical procedure including the patient's spinal cord.

The term "superficial" as used herein has the meaning, a directional term that indicated one structure is located more externally than another, or closer to the surface of the body.

The term "transverse" as used herein has the meaning, situated or extending across an object or an axis.

The term "vertebra" as used herein has the meaning, a bone or object that forms part of the spinal column. The vertebra could be composed of bone or it can be an implant formed from any variety of materials that would be useful to replace bone such as titanium, stainless steel, or other metallic or non-metallic compounds.

The term "withdrawal" as used herein has the meaning, the action of removing or taking away something for a particular location.

Until now, traditional cryotherapy treatments were invasive, and used large complicated machines. A new generation of cryo-needles has revolutionized the delivery of cryoanalgesia. One example is the lovera system by Myoscience.

With cryo-needle systems, doctors are able to deliver precise, controlled doses of cold temperature only to the targeted nerve through a handheld device. This needle-based procedure is safe, and does not damage or destroy the surrounding tissue.

These cryo-needle based treatments use the body's natural response to cold to treat peripheral nerves and immediately reduce pain—without the use of drugs. Treated nerves are temporarily stopped from sending pain signals for a period of time, followed by a restoration of function.

Cryo-needle therapies work by applying targeted cold to a peripheral nerve. A precise cold zone is formed under the skin—cold enough to immediately prevent the nerve from sending pain signals without causing damage to surrounding structures. The effect on the nerve is temporary, providing pain relief until the nerve regenerates and function is restored.

Cryo-needle therapies generally do not require further injection of any substance such as drugs, opioids or narcotics. The effect of this treatment is immediate and can last weeks to several months depending on the multiple factors, including the patients anatomy and pain tolerance. In one study, a majority of the patients suffering from osteoarthritis of the knee have experienced pain and symptom relief beyond 150 days." See also, Radnovich, R. et al. "Cryoneurolysis to treat the pain and symptoms of knee osteoarthritis: a multicenter, randomized, double-blind, sham-controlled trial." Osteoarthritis and Cartilage (2017) p 1-10. (incorporated herein by reference) Cryo-needle therapies use FDA (Food and Drug Administration) approved devices having needles with distal ends that create ice balls, allowing targeted nerves to be stunned inhibiting transmission of pain signals. The procedure is completely reversible weeks to months later.

Cryo-needle therapy technology has allowed tremendous pain control for orthopedic procedures such as total knee and total hip replacement. Freezing the sensory skin nerves of the anterior thigh for total knee replacement and the lateral thigh for hip replacement has resulted in significant drops in opioid need and postoperative pain scores. Similar results are available for sensory freezing the posterior cutaneous nerves of the spine. Freezing cutaneous nerves alone may not provide sufficient pain relief. We have supplemented the cryoanalgesia treatment with a nerve block called an Erector Spinae Block. Erector spinae blocks are generally placed by physicians, for example anesthesiologists, using ultrasound. Erector spinae blocks may also be placed by surgeons using guided navigation surgery software. Using cryo-needle technology for previously untried lumbar fusion spine procedures provides surprising success. Other possible applications include anesthesia pain blocks for chronic pain, thus avoiding more invasive epidural steroid injections. Routine lumbar discectomy and laminectomy patients may also receive cryo-needle treatment at the end of surgeries. More complex cervical and thoracic spine applications are also possible.

Sensory nerves that are targeted for pain relief may innervate anterior, posterior, and/or lateral regions of the body. In certain embodiments, the current disclosure provides methods of training for anesthetizing a patient undergoing surgical procedures at or in anterior, posterior, and/or lateral regions of the body.

The lateral region of the body includes lateral portions of the thorax as well as extremities, hips, knees, arms, elbows, shoulders, hands, feet, and legs.

In certain embodiments, the present disclosure provides for an anthropomorphic phantom configured to simulate one or more structures and/or regions of a human body. In some forms an anthropomorphic phantom of the present disclosure is configured to simulate: skin, muscle, nerves, bones, chest wall, breast, esophagus, trachea, lungs, pleura, diaphragm, mediastinum, heart, pericardium, great vessels with and without pump oxygenator, anterior cervical spine, anterior thoracic spine, anterior lumbar spine, upper anterior abdominal wall including hernias (lumbar, ventral, umbilical, incisional, diaphragmatic, omphalocele), anterior major abdominal blood vessels, spleen, liver, pancreas, liver, anterior lower abdomen wall (hernias), kidney uterus, bladder, adrenal glands, prostate, vagina, and/or anterior pelvis. Surgical procedures which may be performed in conjunction with the anterior region of the body in accordance with the present disclosure include, for example: thoracoscopy, thoracotomy, transplant, anterior intraperitoneal procedures such as spleen, liver, pancreas, liver transplant, and/or gastric bypass, abdominoperineal resection, hysterectomy, pelvic exenteration, nephrectomy, adrenalectomy, renal transplant, prostatectomy, and/or vaginal procedures.

In certain embodiments, the present disclosure provides for an anthropomorphic phantom configured to simulate one or more structures and/or regions of a human body. In some forms an anthropomorphic phantom of the present disclosure is configured to simulate: cervical spine, thoracic spine, lumbar spine, sacral spine, extensive complex spine, and/or spinal cord instrumentation cervical spine to sacral spine In certain embodiments, the cryo-needle comprises two or more needle ends configured to cool surrounding patient tissue. In some forms, the two or more needle ends are configured in a generally linear array.

In accordance some forms of practicing the disclosed methods, an imageable cryo-needle is used, such that the erector spinae block and/or the cryo-needle are placed using guidance from a medical imaging device. Alternatively, or in combination with the above, guided surgical navigation software has developed and evolved over the past two decades. For example, the Stealth surgical navigation system by Medtronic. Today, surgeons (e.g. neurosurgeon or orthopedic spine surgeon) rely on proper software for complex spine procedures. Evolution of surgical practice has led to innovations like CT/MRI guided fusions, passive markers, touch screen displays and laser surface registration. Postoperative multimodal pain pathways have been marginal at best for controlling severe pain associated with these complex spine procedures. Regional anesthesia pain blocks have not been commonly practiced with spine surgery for multiple reasons. For example, guided navigation requires sensory monitoring of spinal cord signals throughout the procedure. Local anesthetics would, or may, prevent or impede sensory monitoring. Thus, preoperative pain blocks using conventional local anesthetics before surgery is not normally possible. In addition, reducing postoperative pain with local anesthetic pain blocks may mask inadvertent surgical epidural hematoma.

Figure 3:
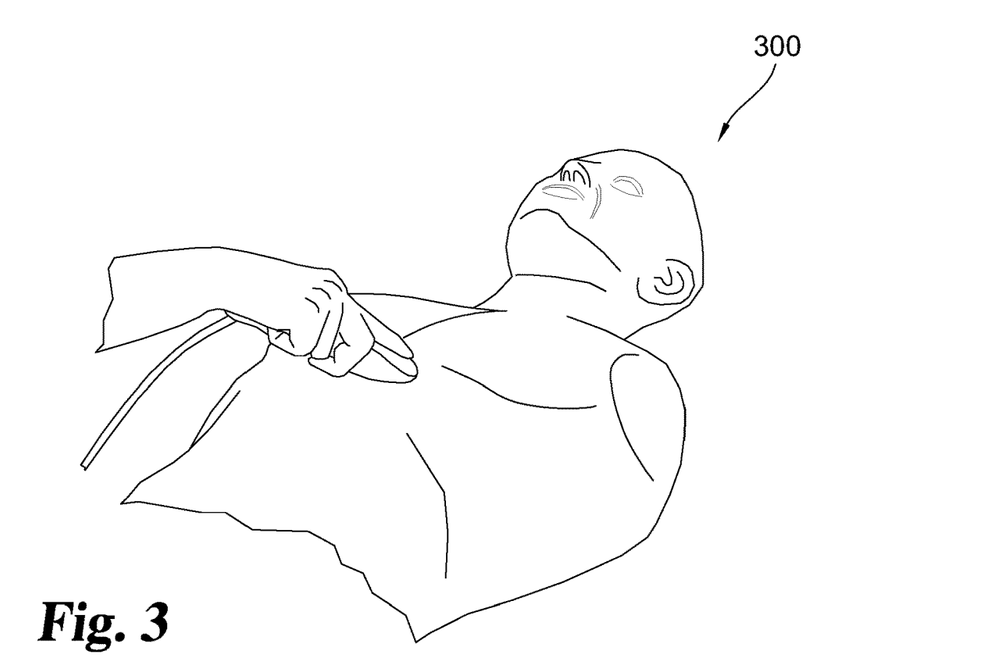
FIG. 3 is one example of an anthropomorphic cryoneurolysis training phantom.

In some forms, the present disclosure provides for anthropomorphic phantoms having the look and feel of human tissue during a cryo-needle therapy and related procedures as disclosed herein. Anthropomorphic phantoms as used herein may comprise all or part of a simulated patient. For example, in some forms the present disclosure provides for anthropomorphic phantoms configured to simulate one or more anatomical structures of a mammal, preferably a human. A full torso ultrasound simulator model 300 is seen in FIG. 3. In some forms larger models, such as the full torso model shown in FIG. 3, have the ability to be partitioned into smaller subunits. Such module designs are advantageous when, for example, certain facilities may only desire a portion of the model, such as the abdomen, thorax, spine, and/or lower extremities.

Current simulator models are ultrasound compatible for traditional regional anesthesia nerve blocks and may be configured to use commercially available needles and local anesthetic solutions for training. Traditional regional anesthesia nerve blocks target compartments and relatively large volumes of local anesthetic flood the intended site. Cryoneurolysis needles on the other hand, are dull and require an introducer port opening created by a sharp needle. Target nerves for cryoneurolysis tend to be smaller and more superficial to the surface than those targeted by traditional anesthesia nerve blocks. Thus, precise ultrasound skill is required to place the dull cryoneurolysis needle between fascial planes adjacent to the target nerve. This in one example a sharp needle having a peel-away sheath is used to access through an outer layer.

In certain embodiments, the present disclosure provides a method of using an anthropomorphic phantom, the method comprising the steps of visualizing a target nerve, introducing a first needle through an outer layer to reach the target nerve, removing the first needle, and introducing a second needle to the target nerve. In certain embodiments, the visualizing comprises ultrasound visualization. In certain embodiments the introducing the first needle comprises piercing the skin of a patient or the simulated skin of an anthropomorphic phantom. In certain embodiments, the first needle comprises a peel-away sheath, which allows for access of the second needle to the target nerve. In preferred embodiments, the second needle comprises a cryoneurolysis needle. In some forms, the second needle (e.g. cryoneurolysis needle) is advanced further into the patient tissue to reach the target nerve. In certain embodiments, the method further comprises activating the cryoneurolysis needle to cause cooling of the target nerve.

Anthropomorphic phantoms of the present disclosure are configured to simulate anatomical tissues. In certain embodiments, the anthropomorphic phantom of the present disclosure comprises one or more materials configured to simulate one or more soft tissues such as skin, fascia, vasculature, nerve, muscle, and or adipose tissues. In certain embodiments, such materials are configured to mimic the tactile properties of natural tissues, including puncture resistance. In some forms, such materials are configured to mimic the tensile strength characteristics of natural tissue. In some forms, such materials are configured to mimic the imageable characteristics of natural tissues to simulate sonographic characteristics of natural tissues. In this way, the anthropomorphic phantom may comprise one or more thermoplastic elastomers. Exemplary thermoplastic elastomers include highly plasticized styrene, ethylene, butylene, and/or styrene block copolymers. In this way, anthropomorphic phantoms of the present disclosure may be formed by heating and/or mixing one or more chemical compositions and pouring the heated composition into a mold to form a simulated anatomical structure. For example, in some forms anthropomorphic phantoms of the present disclosure may be formed by heating and/or mixing one or more thermoplastic elastomers and pouring the heated composition into a mold to form a simulated anatomical structure. In certain embodiments, various pigments may also be added to the material to differentiate tissue structure and/or simulate natural tissue. In certain embodiments, one or more scattering agents are added to the thermoplastic compositions. The scattering agent(s) is selected to confer natural sonographic characteristics to the anthropomorphic phantom. Examples of scattering agents include talcum powder, graphite powder, and/or glass spheres.

In some forms, the anthropomorphic phantom of the present disclosure may comprise a simulated fascial plane. In certain embodiments, the simulated fascial plane is associated with one or more other materials simulating structures superficial and/or deep to the simulated fascial plane. In some forms, the simulated fascial plane has a tensile strength greater than one or more surrounding materials. This allows for tactile feedback to a user when penetrating the anthropomorphic phantom so as to indicate arrival of the instrument at or through the fascial plane.

In certain embodiments, the anthropomorphic phantom of the present disclosure includes one or more simulated nerves. In some forms, the simulated nerve(s) is embedded in one or more other materials simulating tissue structures surrounding the simulated nerve. In accordance with certain inventive variants, the simulated nerve comprises a sensor configured to detect a signal from a Cryoneurolysis training needed. In certain embodiments, the simulated nerve is configured to detect a change in temperature, for example the presence of an ice ball formed by a cryo-needle sufficiently near the simulated nerve so as to inhibit a natural nerve. In this way, anthropomorphic phantoms provided by the present disclosure may further comprise a controller responsive to the simulated nerve sensor and configured to indicate a status of the detected signal. For example in certain embodiments, an audible or visible signal is produced upon activation of the sensor signifying sufficient inhibition of the nerve. In certain embodiments, the controller is electrically connected to the sensor. In some forms, the sensor is configured to detect the duration of the signal.

In certain embodiments the cryoneurolysis training device of the present disclosure comprises a hand piece having a training cryoneurolysis needle attached thereto, the hand piece operably connected to a display such as a monitor. The hand piece is configured to send a signal to the display when the phantom target structure is contacted by the training cryoneurolysis needle. Thus in certain embodiments, the display is configured to present a signal to confirm the paresthesia experienced during cryoneurolysis on living patients. In some forms, the positive signal persists while the target nerve is actively cooled, thus a target duration of treatment can be simulated. In certain embodiments, the target nerve is cooled for at least thirty seconds, preferably at least forty-five seconds, even more preferably at least sixty seconds.

In accordance with certain inventive variants, the present disclosure provides for an anthropomorphic phantom for use with cryoneurolysis procedure training for surgical procedures in and around the knee joint. Exemplary procedures with which the anthropomorphic phantom of the present disclosure may be used include but are not limited to: knee replacement (e.g. knee arthroplasty, or total knee replacement), partial knee replacement, patella replacement or repair, complex knee replacement, removal or repair of meniscus, anterior cruciate ligament (ACL) surgery, removal or repair of synovial tissues, removal or repair of damaged articular cartilage, removal of loose bone fragments of bone or cartilage, and/or treatment of sepsis in or around the knee joint.

Figure 1:
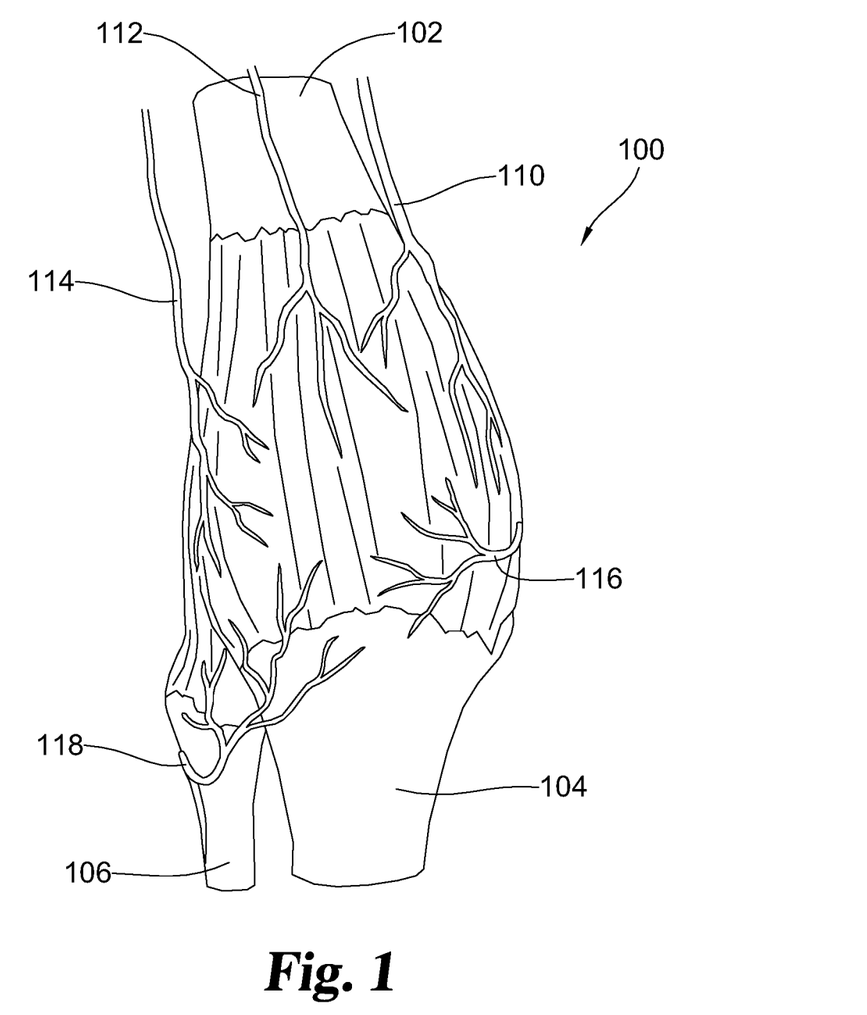
FIG. 1 is one example of a total knee anthropomorphic cryoneurolysis training phantom.

In certain embodiments, the present disclosure provides for an anthropomorphic phantom for use with cryoneurolysis procedure training for total knee arthroplasty. With reference to FIG. 1, in certain embodiments, the present disclosure provides an anthropomorphic phantom 100 configured to simulate a human knee. In accordance with some forms, an anthropomorphic phantom may comprise one or more simulated bones, for example a simulated femur 102, a simulated tibia 104, and/or a simulated fibula 106. In certain embodiments, an anthropomorphic phantom may include a simulated patella. In the illustrated embodiment, the simulated bones are partial bone segments configured to allow training on the knee joint. It is within the scope of the disclosure to provide anthropomorphic cryoneurolysis training phantoms having complete simulated bone structures as well. In accordance with some forms, an anthropomorphic phantom may comprise one or more simulated nerves, for example a simulated medial femoral cutaneous nerve 110, a simulated intermediate femoral cutaneous nerve 112, a simulated lateral femoral cutaneous nerve 114, a simulated infra patellar branch of the saphenous nerve 116, a simulated common peroneal nerve 118, a simulated posterior femoral cutaneous nerve, a simulated obturator nerve, a simulated tibial nerve, and/or a simulated nerve to the vastus medialis. As discussed herein, anthropomorphic cryoneurolysis training phantoms of the present disclosure may also include simulated soft tissue structures associated with the simulated bone and/or nerve structures. For example, in certain embodiments an anthropomorphic cryoneurolysis training phantom may include a knee joint comprising: simulated ligaments, simulated muscle tissue, simulated fascial tissue, simulated adipose tissue, simulated cartilage, simulated vasculature, and/or simulated dermal tissue. As discussed herein these simulated soft tissue may be configured to appear natural under ultrasound guidance and to provide natural physical feedback to the user. Thus in certain embodiments the present disclosure provides materials and methods for anesthesia training of a total knee arthroplasty including percutaneously accessing one or more of the listed structures with a cryoneurolysis needle. In certain embodiments, cryoneurolysis is applied once the target structure (e.g. nerve) is accessed.

Figure 2:
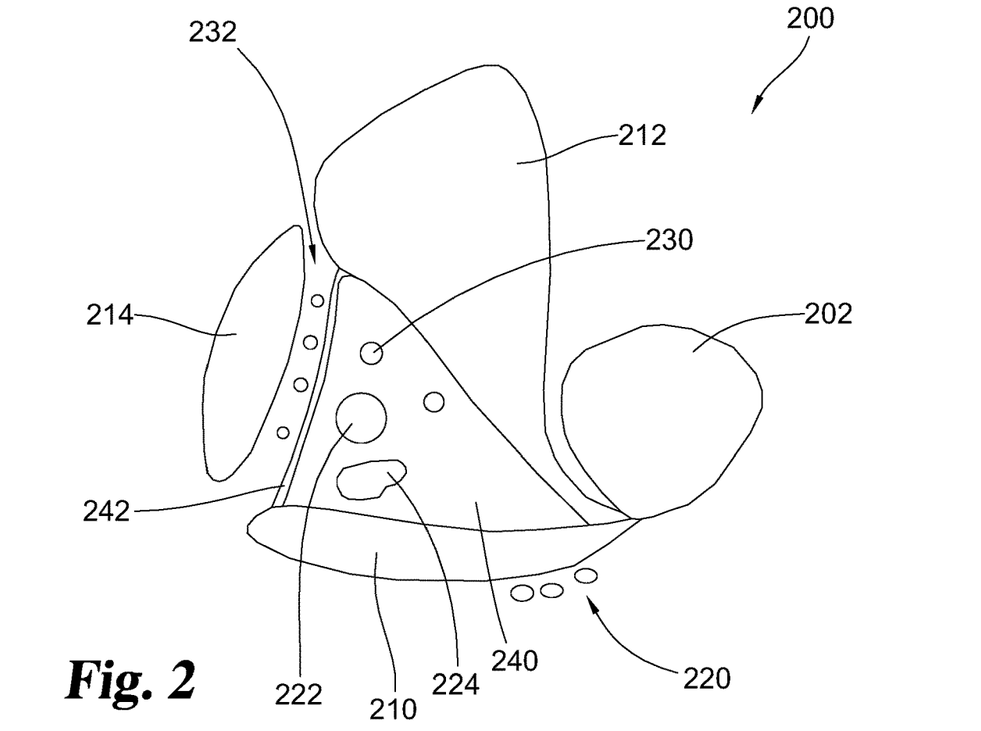
FIG. 2 is a cross-sectional view of one example of an anthropomorphic cryoneurolysis training phantom.

FIG. 2 is a cross-sectional view of one example of an anthropomorphic cryoneurolysis training phantom 200. The anthropomorphic cryoneurolysis training phantom of the illustrated embodiment contains simulated features useful, for example, for training cryoneurolysis for a total knee procedure including the femoral triangle 240. Certain embodiments include simulated connective tissues, for example, the fibrous roof 242 of the femoral triangle. In certain embodiments, anthropomorphic cryoneurolysis training phantoms may include simulated bone structures. Simulated structures of the illustrated embodiment include simulated femur 202. In certain embodiments, anthropomorphic cryoneurolysis training phantoms may include simulated muscle tissue. For example, the illustrated embodiment comprises a simulated adductor longus 210, a simulated vastus medialis 212, and a simulated Sartorius 214. In certain embodiments, anthropomorphic cryoneurolysis training phantoms may include simulated vasculature. For example, the illustrated embodiment comprises simulated vessels of the profunda femoris 220, a simulated femoral artery 222, and a simulated femoral vein 224. In certain embodiments, anthropomorphic cryoneurolysis training phantoms may include simulated nerves. For example, the illustrated embodiment comprises a simulated saphenous nerve to the vastus medialis 230, and simulated nerves of the subsartorial plexus 232.

In certain embodiments, the present disclosure provides for an anthropomorphic phantom for use with cryoneurolysis procedure training for posterior knee. In certain embodiments, the anthropomorphic phantom described herein includes the medial knee epicondyle. Thus in certain embodiments the present disclosure provides materials and methods for anesthesia training of a posterior knee procedure including percutaneously accessing the medial knee epicondyle with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for total hip arthroplasty. In certain embodiments, the anthropomorphic phantom described herein includes the lateral femoral cutaneous nerve. Thus in certain embodiments the present disclosure provides materials and methods for anesthesia training of a total hip arthroplasty including percutaneously accessing the lateral femoral cutaneous nerve with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for shoulder surgery. In certain embodiments, the anthropomorphic phantom described herein includes the supra scapular nerve. Thus in certain embodiments the present disclosure provides materials and methods for anesthesia training of a shoulder surgery including percutaneously accessing the lateral supra scapular nerve with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for spinal surgery, in particular for erector spinea blocks. In certain embodiments, the anthropomorphic phantom described herein includes the spinal nerve, including the medial dorsal rami. Thus in certain embodiments the present disclosure provides materials and methods for anesthesia training of a spinal surgery including percutaneously accessing the dorsal rami with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for an ankle block. In certain embodiments, the anthropomorphic phantom described herein includes one or more of the following structures: peroneal nerve, posterior tibial nerve, sural nerve, and/or saphenous nerve. Thus in certain embodiments the present disclosure provides materials and methods for anesthesia training of an ankle block including percutaneously accessing one or more of the listed structures with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for abdominal surgery, in particular an abdomen-tap block, transversalis fascia block, and/or ilio-inguinal nerve block. Thus in certain embodiments the present disclosure provides materials and methods for anesthesia training of an abdominal surgery including percutaneously accessing the target nerve with a cryoneurolysis needle. In certain embodiments, cryoneurolysis is applied once the target structure (e.g. nerve) is accessed.

In certain embodiments, the present disclosure provides for an anthropomorphic phantom for use with cryoneurolysis procedure training for surgeries of the anterior and posterior chest wall, including breast surgery, thoracotomy, cardiac surgery, and/or upper abdominal surgery. Thus in certain embodiments the present disclosure provides materials and methods for anesthesia training of an abdominal surgery including percutaneously accessing the target structure (e.g. serrates anterior, and/or intercostal nerves) with a cryoneurolysis needle. In certain embodiments, cryoneurolysis is applied once the target structure (e.g. nerve) is accessed.

Listing of Certain Embodiments

The following provides an enumerated listing of some of the embodiments disclosed herein. It will be understood that this listing is non-limiting, and that individual features or combinations of features (e.g. 2, 3 or 4 features) as described in the Detailed Description above can be incorporated with the below-listed Embodiments to provide additional disclosed embodiments herein.

1. An anthropomorphic phantom for use with cryoneurolysis procedure training, comprising:
   a phantom body shaped to simulate a human anatomical structure, the phantom body comprising a first material configured to simulate human soft tissue;
   a simulated nerve embedded within the first material; and
   a simulated fascial plane embedded within the first material superficial to said simulated nerve, the simulated fascial plane being distinctly imageable to simulate sonographic characteristics of human fascial planes.
2. The anthropomorphic phantom of embodiment 1, wherein said simulated fascial plane has a tensile strength greater than said first material.
3. The anthropomorphic phantom of any one of the preceding embodiments, wherein said first material comprises a chemical composition capable of being heated and poured into a mold to form a simulated anatomical structure.
4. The anthropomorphic phantom of embodiment 3, wherein said chemical composition comprises thermoplastic elastomers that are heated, mixed together and then poured into said mold.
5. The anthropomorphic phantom of embodiment 4, further comprising a pigment mixed with said thermoplastic elastomers.
6. The anthropomorphic phantom of any one of the preceding embodiments, further comprising at least one scattering agent embedded in the first material to simulate sonographic characteristics of a human soft tissue.
7. The anthropomorphic phantom of any one of the preceding embodiments, further comprising at least one scattering agent embedded in the simulated nerve to simulate sonographic characteristics of a human nerve.
8. The anthropomorphic phantom of any one of the preceding embodiments, wherein the simulated nerve comprises a sensor configured to detect a signal from a cryoneurolysis training needle.
9. The anthropomorphic phantom of embodiment 8 wherein the signal comprises a change in temperature caused by the cryoneurolysis training needle.
10. The anthropomorphic phantom of any one of embodiments 8 or 9, further comprising a controller responsive to said sensor, the controller configured to indicate a status of the detected signal.
11. The anthropomorphic phantom of embodiment 10, wherein said controller is electrically connected to said sensor.
12. The anthropomorphic phantom of any one of embodiments 8 through 11, wherein said sensor is configured to detect a duration of the signal.
13. The anthropomorphic phantom of any one of the preceding embodiments, wherein said phantom body is shaped to simulate a human knee.
14. The anthropomorphic phantom of any one of the preceding embodiments, wherein said phantom body is shaped to simulate a human thorax.
15. A method of using an anthropomorphic phantom for cryoneurolysis training, the method comprising the steps of:
    visualizing a target nerve; and
    introducing an introducer needle through an outer layer of the anthropomorphic phantom to reach the target nerve, wherein the introducer needle provides an access path to the target nerve; and
    introducing a cryoneurolysis needle through the access path to the target nerve.
16. The method of embodiment 15, further comprising:
    activating the cryoneurolysis needle to cause cooling of the target nerve.
17. The method of any one of embodiments 15 to 16, wherein said visualizing comprises ultrasound visualization.
18. The method of any one of embodiments 15 to 17, wherein said introducer needle comprises a peel away sheath.

The invention may include any one or more articles or devices made by any of the claimed methods and/or may by different methods but with a claimed composition.

The language used in the claims and the written description and in the above definitions is to only have its plain and ordinary meaning, except for terms explicitly defined above. Such plain and ordinary meaning is defined here as inclusive of all consistent dictionary definitions from the most recently published (on the filing date of this document) general purpose Webster's dictionaries and Random House dictionaries.

While the invention has been illustrated and described in detail in the drawings and foregoing description, the same is to be considered as illustrative and not restrictive in character, it being understood that only the preferred embodiment has been shown and described and that all changes, equivalents, and modifications that come within the spirit of the inventions defined by following claims are desired to be protected. All publications, patents, and patent applications cited in this specification are herein incorporated by reference as if each individual publication, patent, or patent application were specifically and individually indicated to be incorporated by reference and set forth in its entirety herein.

The invention claimed is:

1. An anthropomorphic phantom for use with cryoneurolysis procedure training, comprising:
   a phantom body shaped to simulate a human anatomical structure, the phantom body comprising a first material configured to simulate human soft tissue;
   a simulated nerve embedded within the first material, and wherein the simulated nerve comprises a sensor configured to detect a signal from a cryoneurolysis training needle, and wherein the signal comprises a change in temperature caused by the cryoneurolysis training needle.

2. The anthropomorphic phantom of claim 1, wherein said first material comprises a chemical composition capable of being heated and poured into a mold to form a simulated anatomical structure.

3. The anthropomorphic phantom of claim 2, wherein said chemical composition comprises thermoplastic elastomers that are heated, mixed together and then poured into said mold.

4. The anthropomorphic phantom of claim 3, further comprising a pigment mixed with said thermoplastic elastomers.

5. The anthropomorphic phantom of claim 1, further comprising at least one scattering agent embedded in the first material to simulate sonographic characteristics of a human soft tissue.

6. The anthropomorphic phantom of claim 1, further comprising at least one scattering agent embedded in the simulated nerve to simulate sonographic characteristics of a human nerve.

7. The anthropomorphic phantom of claim 1, wherein change in temperature caused by the cryoneurolysis training needle comprises a colder temperature relative to the surrounding material.

8. The anthropomorphic phantom of claim 7, further comprising a controller responsive to said sensor, the controller configured to indicate a status of the detected signal.

9. The anthropomorphic phantom of claim 8, wherein said controller is electrically connected to said sensor.

10. The anthropomorphic phantom of claim 1, wherein said sensor is configured to detect a duration of the signal.

11. The anthropomorphic phantom of claim 1, wherein said phantom body is shaped to simulate a human knee.

12. The anthropomorphic phantom of claim 1, wherein said phantom body is shaped to simulate a human thorax.

13. A method of using an anthropomorphic phantom for cryoneurolysis training, the method comprising the steps of:

visualizing a target nerve, the target nerve comprising a simulated nerve embedded within a phantom body shaped to simulate a human anatomical structure, the phantom body comprising a first material configured to simulate human soft tissue;

introducing a cryoneurolysis needle through the first material to the target nerve; and activating the cryoneurolysis needle to cause cooling of the target nerve.

14. The method of claim 13, wherein said visualizing comprises ultrasound visualization.

15. The method of claim 13, wherein the simulated nerve comprises a sensor configured to detect a signal from a cryoneurolysis training needle.

16. The method of claim 13, comprising:
detecting a change in temperature of said target nerve.

* * * * *